(12) United States Patent
Li et al.

(10) Patent No.: US 7,862,585 B2
(45) Date of Patent: Jan. 4, 2011

(54) TISSUE REPAIR DEVICE AND FABRICATION THEREOF

(75) Inventors: Zhigang Li, Hillsborough, NJ (US);
Kevin Cooper, Flemington, NJ (US);
Raymond S. Shissias, Iselin, NJ (US);
Qiang Zhang, Annandale, NJ (US)

(73) Assignee: Johnson & Johnson, New Brunswick, NJ (US)

( * ) Notice: Subject to any disclaimer, the term of this patent is extended or adjusted under 35 U.S.C. 154(b) by 726 days.

(21) Appl. No.: 11/159,536

(22) Filed: Jun. 23, 2005

(65) Prior Publication Data

US 2006/0293674 A1 Dec. 28, 2006

(51) Int. Cl.
*A61B 17/04* (2006.01)
(52) U.S. Cl. .................... 606/232; 606/301
(58) Field of Classification Search ........... 606/161, 606/72–74, 77, 61, 301, 304, 308, 310, 316, 606/601, 232, 224–228; 623/13–14; 24/1–30, 24/68 R–711.5
See application file for complete search history.

(56) References Cited

U.S. PATENT DOCUMENTS

| | | | |
|---|---|---|---|
| 1,079,881 A * | 11/1913 | Reagles | 403/180 |
| 4,745,968 A * | 5/1988 | Demos | 165/185 |
| 5,152,945 A | 10/1992 | Thicthener et al. | |
| 5,674,286 A | 10/1997 | D'Alessio et al. | |
| 5,702,397 A * | 12/1997 | Goble et al. | 606/72 |
| 5,964,783 A | 10/1999 | Grafton et al. | |
| 6,083,522 A | 7/2000 | Chu et al. | |
| 6,235,869 B1 * | 5/2001 | Roby et al. | 528/354 |
| 6,641,597 B2 | 11/2003 | Burkhart et al. | |
| 2002/0087190 A1 | 7/2002 | Benavitz et al. | |
| 2003/0187444 A1 | 10/2003 | Overaker et al. | |
| 2003/0187446 A1 | 10/2003 | Overaker et al. | |
| 2004/0049194 A1 * | 3/2004 | Harvie et al. | 606/72 |
| 2004/0127907 A1 * | 7/2004 | Dakin et al. | 606/72 |
| 2005/0070905 A1 * | 3/2005 | Donnelly et al. | 606/72 |
| 2005/0119696 A1 * | 6/2005 | Walters et al. | 606/228 |
| 2005/0119698 A1 * | 6/2005 | Martinek | 606/232 |

FOREIGN PATENT DOCUMENTS

EP 0664198 6/1999

* cited by examiner

*Primary Examiner*—Anhtuan T Nguyen
*Assistant Examiner*—Amy Lang
(74) *Attorney, Agent, or Firm*—Roberts, Mlotkowski, Safran & Cole, P.C.

(57) ABSTRACT

A device for use in tissue repair, a method of using the device in a surgical procedure and a method of making the device. The device is an assembly of a cannulated anchor with a cord passed through it, and a stopper to prevent the cord from passing back through the anchor.

21 Claims, 3 Drawing Sheets

TISSUE REPAIR DEVICE AND FABRICATION THEREOF

FIELD OF THE INVENTION

The present invention relates to medical devices. More specifically medical devices for use in tissue repair, surgical procedures for repairing tissue using such devices, and a method of making the devices.

BACKGROUND OF THE INVENTION

There are many applications in the field of orthopaedics for medical devices used in surgical procedures, wherein there is a requirement to anchor at least a section of a cord (e.g., a tape or a surgical suture) within a bone bore hole. A solid and secure attachment between the cord and anchoring components of anchor devices is essential to the success of the device. Such conventional devices include vertebral straps, suture anchors, and suture staples.

Conventionally known methods for attaching or securing cords to anchoring components include insert molding, passing the cords through eyelets or small holes in the anchoring components, compressing the cord between surfaces of the device, etc. Although generally satisfactory for their intended purpose, there may be certain disadvantages attendant with the use of such attachment methods. For example, a disadvantage of the insert molding method may be low pull-out strength of the cord from the anchoring component. This is believed to be caused by the difficulty in general, conventional compression molding processes to form a secure attachment between the cord and anchoring components. When using an eyelet or small hole, the hole or the eyelet are related to the removal or absence of material from the anchoring component which may, in some cases, result in mechanical strength lost, or it may be difficult or not possible to place a hole or an eyelet in or on the anchoring component due to a low profile configuration or limited space.

Accordingly, there is a need in this art for novel medical devices for use in tissue fixation, wherein the devices have a flexible cord attached.

SUMMARY OF THE INVENTION

The tissue repair device of the present invention overcomes the above stated limitations by providing a device having a cannulated anchor member, a cord that passes through the anchor cannulation, a rod member, and a stopper to prevent the cord from passing back through the anchor cannulation, wherein the rod member is passed through and end of the cord and imbedded within the stopper. The stopper member is molded about the cord end containing the rod member. This enhances the attachment strength of the cord to the stopper.

Another aspect of the present invention is a method of using the previously-described device in a surgical procedure.

Yet another aspect of the present invention is a method of manufacturing the tissue repair devices of the present invention.

The novel tissue repair devices having cannulated anchor members, cords and stopper members overcome the disadvantages of the prior art by providing secure fixation and minimizing or eliminating the possibility of the cord separating from the anchor member.

These and other features and advantages of the present invention will become more apparent from the following description and accompanying drawings.

DETAILED DESCRIPTION OF THE INVENTION

The tissue repair device of the present invention is a device that has a cannulated anchor member through which a cord passes, and a stopper that prevents the cord from passing back through the anchor. The stopper is molded around an end of the cord and a rod is passed through the cord and imbedded within the stopper. This enhances the attachment strength of the cord to the stopper.

Figure 1:
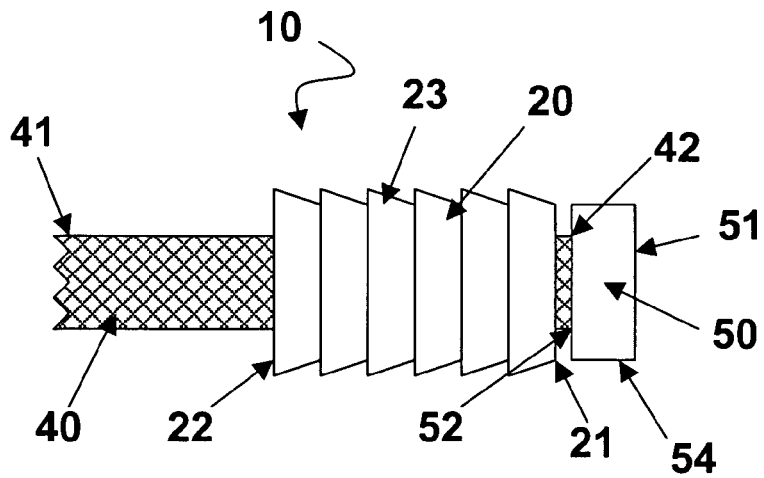
FIG. 1 is a side view of an embodiment of a tissue repair device of the present invention.

An embodiment of the device 10 of the present invention is seen in FIGS. 1 and 2. Device 10 is seen to have a cannulated anchor member 20, a cord 40, a rod member 60 and a stopper 50. Anchor member 20 has first end 21 and second end 22, and outer surface 23. A plurality of ridge members 24 are seen to extend out from anchor member 20 to assist in securing the anchor member 20 in tissue. If desired, other types of conventional tissue securement members may be utilized including screw threads, spikes, projections having various geometric configurations such as pyramidal, cylindrical, hemispherical, etc. Anchor member 20 is also seen to have longitudinal passage 30 extending therethrough and to also have opening 31 in first end 21 and opening 32 in second end 22, both openings are in communication with passage 30. Longitudinal passage 30 may have a variety of cross-sections including circular, square, rectangular, oval and the like. Cord 40 is seen to be an elongated flexible member, preferably made from a plurality of fibers although a cord made from a single element may be used. Examples of cords 40 that may be used in the devices 10 of the present invention include conventional sutures, tapes, ropes, and the like. Cord 40 is seen to have first end 41 and second end 42.

Figure 2A:
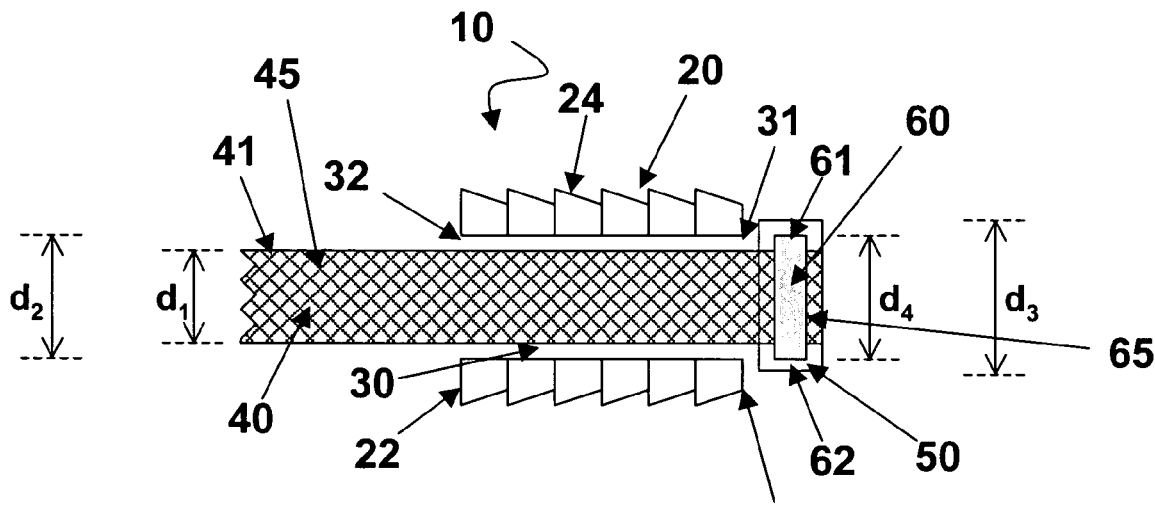
FIG. 2a is a cross-sectional view of the device of FIG. 1.
Figure 2B:
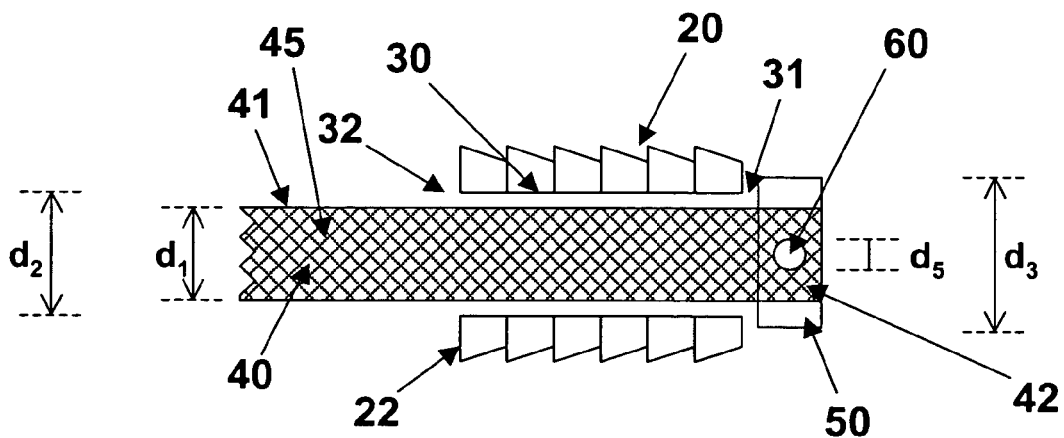
FIG. 2b is a cross-sectional view of the device of FIG. 1 rotated 90°.

As shown in FIGS. 2a and 2b, rod member 60 is embedded in cord 40, and within stopper 50. Rod 60 has dimensions $d_4$ and $d_5$ where dimension $d_4$ is larger than dimension $d_1$ of cord 40 so that rod 60 passes completely through cord 40. Stopper member or stopper 50 is seen to be a substantially disc-like member having top 51, bottom 52 and side 54. The stopper member 50 may have a variety of geometric configuration including spheres, cubes, cylinders, pyramids, and combinations thereof and the like. As mentioned previously above, anchor member 20 is cannulated and has longitudinal passage 30. The maximum dimension of the cross-section of passage 30 has dimension $d_2$ that is sufficient for the through passage of cord 40 (with dimension $d_1$) through anchor member 20. Stopper member 50 has outer dimension $d_3$ sufficiently greater than $d_2$ to effectively prevent it from passing through longitudinal passage 30 of anchor member 20.

Cord 40 is composed of fibers, and may be in any of the forms known in textile technologies. These forms include braids, weaves, and knits. If braided, cord 40 can be in the form of a biaxial, triaxial, or tailored braid, or a braid formed by other known braiding methods. Cord 40 may also consist of a single element, e.g., a strip cut from a polymeric film, etc.

Rod 60 is seen to be a substantially cylindrical member having opposed ends 61 and 62 and outer surface 65. Although shown as having a cylindrical geometry, with a circular cross-section, rod member 60 may have other geometries (triangular, square, rectangular, oval cross-sections) that will function in a similar manner. In addition, if desired, although not shown, the ends 61 and 62 may be rounded or pointed.

Suitable materials from which cannulated anchoring member 20, cord 40 and rod 60 may be formed include biocompatible polymers selected from the group consisting of aliphatic polyesters, polyorthoesters, polyanhydrides, polycarbonates, polyurethanes, polyamides and polyalkylene oxides. They also can be formed from biocompatible metals, glasses or ceramics, or from autograft, allograft, or xenograft bone tissues.

Anchoring member 20, cord 40, and rod 60 further can be made from or include combinations of metals, ceramics, glasses and polymers.

The biocompatible materials can be biodegradable or non-biodegradable. Biodegradable materials, such as polymers, readily break down into small segments when exposed to moist body tissue. The segments then either are absorbed by the body, or passed by the body. More particularly, the biodegraded segments do not elicit permanent chronic foreign body reaction, because they are absorbed by the body or passed from the body, such that no permanent trace or residual of the segment is retained by the body.

In one embodiment, cannulated anchor member 20, cord 40, or rod 60 are made from biodegradable aliphatic polymer and copolymer polyesters and blends thereof. The aliphatic polyesters are typically synthesized in a ring opening polymerization. Suitable monomers include but are not limited to lactic acid, lactide (including L-, D-, meso and D,L mixtures), glycolic acid, glycolide, epsilon-caprolactone, p-dioxanone (1,4-dioxan-2-one), and trimethylene carbonate (1,3-dioxan-2-one).

Several preferred materials for anchor member 20, cord 40, and rod 60 include poly(lactic acid), or PLA, and a copolymer of lactic acid with glycolic acid, or poly(lactide-co-glycolide) (PLGA), in a mole ratio of 95 lactic acid to 5 glycolic acid.

In another embodiment, the materials used to make anchor member 20, cord 40, or rod member 60 will be biodegradable glasses or ceramics comprising mono-, di-, tri-, alpha-tri-, beta-tri-, and tetra-calcium phosphate, hydroxyapatite, calcium sulfates, calcium oxides, calcium carbonates, magnesium calcium phosphates, phospate glasses, bioglasses, and mixtures thereof.

In yet another embodiment, the materials used to make anchor member 20 or rod member 60 can be combinations of biodegradable ceramics and polymers. Composites are prepared by incorporating biodegradable ceramic reinforcements such as particles in a biodegradable polymer matrix.

Stopper member 50 is dimensioned ($d_3$) so that it will not pass through passage 30 dimension $d_2$ of anchoring component 20. Suitable materials from which stopper member 50 may be formed include the biocompatible and biodegradable polymers mentioned above. As with anchor member 20, stopper 50 may be made from combinations of biodegradable ceramics and polymers, or a polymer reinforced with another polymer, such as a short-fiber polymer reinforcing a polymer matrix. The materials used to form stopper 50 must be flowable, so that they may infiltrate and surround fibers 45 of end 42 of cord 30. Preferred materials include thermoplastic biocompatible and biodegradable polymers.

One preferred material for stopper 50 is a copolymer of epsilon-caprolactone with p-dioxanone, or poly(epsilon-caprolactone-co-p-dioxanone), in a mole ratio of 95 epsilon-caprolactone to 5 p-dioxanone.

Anchor member 20 and rod member 60 can be formed by a variety of known, conventional processes. If, for example, these components are made from polymeric materials, they can be formed by extrusion, injection molding, machining, and the like. They may be treated before being assembled for enhanced mechanical properties. One example of such treatments is annealing. Strength is enhanced by increased crystallinity through annealing.

As shown in FIGS. 2a and 2b, rod 60 is passed through the end 42 of cord 40 and imbedded within stopper 50. The imbedding of cord 40 and rod 60 within stopper 50 occurs during the forming of stopper 40 so that stopper 50 is molded about the end 42 of cord 40 and rod member 60.

In a preferred embodiment of the present invention, rod member 60 is passed through one end 42 of cord 40, and both are encapsulated in a thermoplastic polymer via a compression molding process as described herein. In this case, stopper 50 is formed of a thermoplastic polymer that has a lower melting point than the materials that comprise cord 40 and rod 60.

Figure 3:
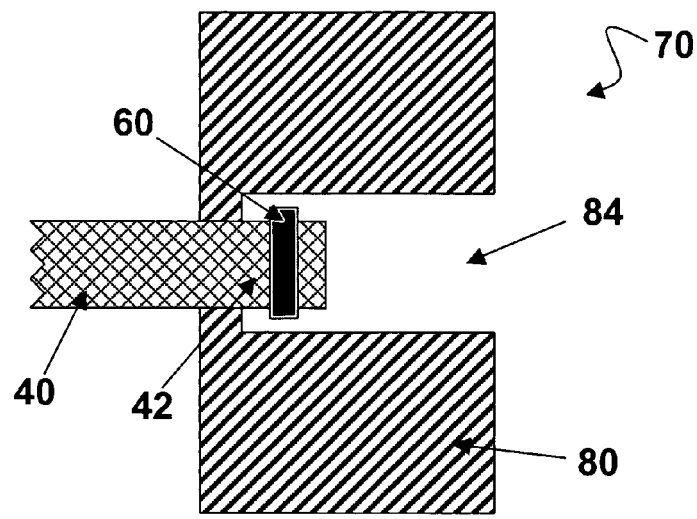
FIG. 3 is a detailed cross-sectional view of a schematic of a molding assembly for forming the stopper assembly of the device of the present invention.

One method of fabricating assembled device 10 of the present invention is schematically shown in FIGS. 3 and 4. In this embodiment, compression molding die assembly 70 is utilized. Die assembly 70 is seen to include a mold 80 having a main cavity 84.

In one embodiment of the fabrication process, rod member 60 is passed through end 42 of cord 40. The end of 42 of cord 40 having rod 60 disposed therethrough is disposed in main cavity 84 of die assembly 70.

Figures 4A, 4B:
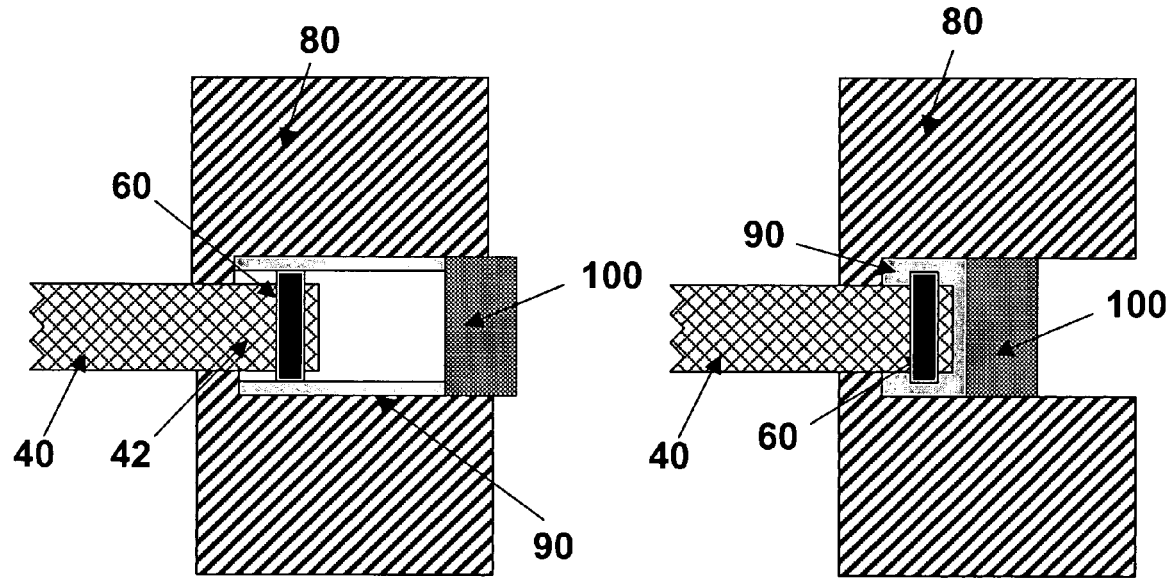
FIG. 4a illustrates molding assembly of FIG. 3 at the onset of the molding process.
FIG. 4b illustrates the molding assembly of FIG. 4a at the conclusion of the molding process.

Next, as shown in FIG. 4a, a prefabricated polymer tube 90, comprised of the polymer that will be used to form stopper 50, is disposed in main cavity 84 of die assembly 70 so that it surrounds the end 42 of cord 40 having the rod 60 disposed therethrough. The tube 90 is prefabricated using extrusion or injection molding or other conventional processes. Conventional plunger 100 is then disposed in main cavity 84 of mold 80 of die assembly 50 as shown.

The entire assembly is then heated to a temperature sufficient to melt prefabricated polymer tube 90. As mentioned previously, polymer tube 90 must be formed of a thermoplastic polymer that has a lower melting point than the materials that comprise rod 60 or cord 40.

Next, plunger 100 is moved in cavity 84 in the direction of cord 40 using a conventional injection molding mechanism driven by an electric motor. The movement of plunger 100 axially in main cavity 84 forces the melted polymer that was tube 90 to flow and embed the rod member 60/cord end 42 combination, and to simultaneously form stopper member 50.

The assembly is cooled, and melted polymer solidifies. After removal from mold 80, the solidified polymer rod 60/cord end 42 combination is trimmed to yield the rod 60/cord end 42/stopper 50 assembly used in the tissue anchoring devices of the present invention.

The attachment strength of cord 40 to stopper 50 in the rod 60/cord end 42/stopper 50 assembly produced according to the present invention is largely enhanced.

The device 10 is assembled by inserting end 41 of cord 40 into opening 31 in end 21 of anchor member 20, and threading cord 40 through passage 30 so that end 41 and a section of cord 40 exit out from opening 32 of end 22.

Figure 5:
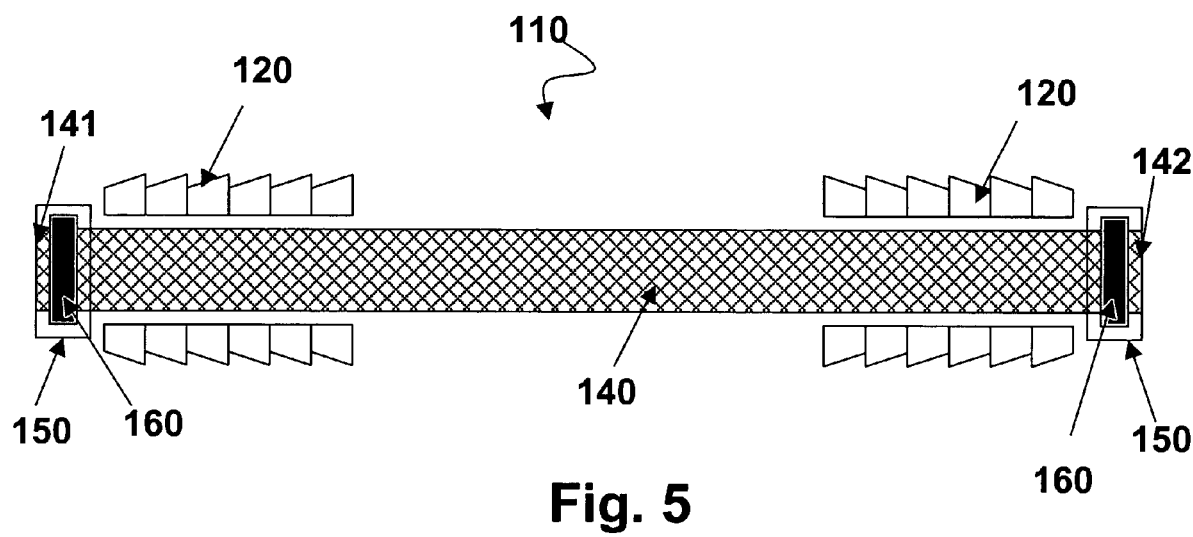
FIG. 5 is a cross-sectional view of a device that has a second anchor member with a first and a second stopper member mounted to the cord in the same manner as the tissue repair device of FIG. 1.

In another embodiment of the tissue repair devices of the present invention shown in FIG. 5, device 110 will have an anchor member 120 mounted to each end of the cord 140 in a similar manner with rods 160 in each end 141 and 142 in stopper members 150 mounted to ends 141 and 142.

The tissue repair devices of the present invention can be used to repair a variety of tissues in various surgical procedures. The devices can be used to approximate tissue, e.g., vertebral repair, approximation of soft tissue to the surface of a bone, etc. Those skilled in this art will appreciate that the anchors of the present invention may also be used with other types of procedures and tissues. The devices may be used in various tissue repair procedures including rotator cuff repair, spinal repair procedures, etc.

The following example is illustrative of the principles and practice of this invention, although not limited thereto.

Example 1

Forming Rod/Cord/Stopper Assemblies

In this example, a general compression molding process was used to form rod 60/cord 40/stopper 50 assembly.

The rod 60 was formed by extruding 95/5 poly(lactide-co-glycolide) (95/5 PLGA) from PURAC (Gorinchem, The Netherlands), with an Inherent Viscosity (I.V) of 2.33 dl/gm (measured in chloroform at 25° C. and a concentration of 0.1 gm/dl) at 200° C. in a DACA Spinline extrusion system. The diameter of rod 60 was 0.635 millimeter. Rod 60 was cut to 0.4 centimeters in length.

The material used to form stopper 50 was 95/5 poly(epsilon-caprolactone-co-p-dioxanone) with an Inherent Viscosity (I.V) of 1.5 dl/gm (measured in chloroform at 25° C. and a concentration of 0.1 gm/dl). The 95/5 poly(epsilon-caprolactone-co-p-dioxanone) was prefabricated into a short tube with dimensions of: OD 0.38 centimeters, ID 0.23 centimeters, and 0.30 centimeters long (by extrusion under an extrusion temperature of 85° C.).

The cord was a three dimensional woven cord made using 95/5 poly(lactide-co-glycolide) (95/5 PLGA) fibers. The fibers are sold under the tradename PANACRYL, (Ethicon, Inc., Somerville, N.J.). The cord was 3D woven with 100 Denier fiber and a diameter of 2 millimeter at Fiber Concepts, Inc. (Conshohocken, Pa.).

Anchor member 20 was made using 95/5 poly(lactide-co-glycolide) by injection molding billets of the material, and machining them into anchors.

The rod was passed through the end of the cord and the assembly was placed into the mold cavity. The prefabricated short tube was placed into the mold so that the end of the cord and the rod were inside the tube. The plunger was then put in place, and the mold was closed and placed into a compression molder (Model 2696, Carver, Inc., Wabash, Ind.). The mold was heated to a temperature of 65° C. for 3 minutes. The plunger was then moved in the direction of the cord and the mold was cooled to a temperature of 25° C. for 3 minutes under compression pressure.

As a control, the same procedure was used with the exception that no rod was passed through the end of the cord. So, in the control there was no rod.

The pullout strength of the two assemblies was tested. Pullout tests were performed using an Instron 4501 test frame. The cord was first loaded on a polyurethane foam block with a pre-drilled hole with diameter of 2.68 mm, which was fixed in place by a special clamp that allows movement in the X-Y plane but not the Z (pulling) direction. The cord end was held tightly by the grips and then a tensile testing procedure was performed with a cross-head rate of 0.1 millimeter/second. The pullout strength of the control was 18 pounds-force (lbf), while that of the assembly with the rod was 32 pounds-force (lbf).

Example 2

Surgical Procedure

A patient is prepared for spinal fusion surgery in a conventional manner. The surgery will fuse one or more levels of the spinal column. The patient is anesthetized in a conventional manner. The tissue repair site is accessed by making an incision through the abdominal cavity and dissecting down to the spinal column. A sterile device of the present invention is prepared for implantation into the patient, the device having anchor members mounted to each end of the cord. The operative site is prepared to receive the anchor members of the repair device by dissecting through the ligamentous structure attached to the vertebral bodies of the spinal column that will be fused. A discectomy procedure is performed to remove the disc of the vertebral level to be fused and a bone graft is inserted into the discs space. A hole is drilled into the vertebral body above and below the disc space. The anchor bodies are then inserted into drilled holes in the adjoining vertebrae to be fused. The cord of the device is used to prevent migration of the bone graft in order to complete the tissue repair. The incision is approximated in a conventional manner using conventional surgical sutures. The incision is bandaged in a conventional manner, thereby completing the surgical procedure.

The novel devices and method of the present invention provide the patient and surgeon with multiple advantages. The advantages include increased pull-out strength and a decoupling of the anchor member from the cord.

Although this invention has been shown and described with respect to detailed embodiments thereof, it will be understood by those skilled in the art that various changes in form and detail thereof may be made without departing from the spirit and scope of the claimed invention.

We claim:

1. A tissue repair device, comprising:
a cannulated anchor member having a longitudinal passage, said passage having first and second open ends;
a flexible cord having a terminal first end and a second end, wherein the cord is slidably mounted in the passage such that the first and second ends of the cord extend, respectively, out from the first and second open ends of the passage, such that the cord is free to slide within said passage;
a rod member, the rod member mounted through the terminal first end of the cord outside of said anchor member; and,
a stopper member separate from said anchor member mounted to the first end of the cord and the rod member outside of said anchor member to prevent the terminal first end of the cord from passing back through the longitudinal passage, wherein the stopper member is molded about and melted to the rod member and the terminal first end of the cord, thereby securing the stopper member to the first end of the cord.

2. The tissue repair device of claim 1, wherein the cord is in a form selected from the group consisting of braid, weave, or knit.

3. The device of claim 2, wherein the cord comprises a braid and is in a form selected from the group consisting of biaxial braid, triaxial braid, or tailored braid.

4. The device of claim 1, wherein the cannulated anchor member, the cord, the rod and the stopper member are formed from biocompatible polymers selected from the group consisting of aliphatic polyesters, polyorthoesters, polyanhydrides, polycarbonates, polyurethanes, polyamides and polyalkylene oxides.

5. The device of claim 1, wherein the cannulated anchor member comprises biocompatible polymers selected from the group consisting of aliphatic polyesters, polyorthoesters, polyanhydrides, polycarbonates, polyurethanes, polyamides and polyalkylene oxides.

6. The device of claim 1, wherein the cord comprises biocompatible polymers selected from the group consisting of aliphatic polyesters, polyorthoesters, polyanhydrides, polycarbonates, polyurethanes, polyamides and polyalkylene oxides.

7. The device of claim 1, wherein the stopper comprises biocompatible polymers selected from the group consisting of aliphatic polyesters, polyorthoesters, polyanhydrides, polycarbonates, polyurethanes, polyamides and polyalkylene oxides.

8. The device of claim 1, wherein the rod comprises biocompatible polymers selected from the group consisting of aliphatic polyesters, polyorthoesters, polyanhydrides, polycarbonates, polyurethanes, polyamides and polyalkylene oxides.

9. The device of claim 1, wherein the cannulated anchor member, the cord, the rod, and the stopper comprise biodegradable aliphatic polymers, copolymers, and blends formed from monomers selected from the group consisting of lactic acid, lactide, glycolic acid, glycolide, epsilon-caprolactone, 1,4-dioxan-2-one, and (1,3-dioxan-2-one).

10. The device of claim 1, wherein the cannulated anchor member comprises biodegradable aliphatic polymers, copolymers, and blends formed from monomers selected from the group consisting of lactic acid, lactide, glycolic acid, glycolide, epsilon-caprolactone, 1,4-dioxan-2-one, and (1,3-dioxan-2-one).

11. The device of claim 1, wherein the cord comprises biodegradable aliphatic polymers, copolymers, and blends formed from monomers selected from the group consisting of lactic acid, lactide, glycolic acid, glycolide, epsilon-caprolactone, 1,4-dioxan-2-one, and (1,3-dioxan-2-one).

12. The device of claim 1, wherein the stopper member comprises biodegradable aliphatic polymers, copolymers, and blends formed from monomers selected from the group consisting of lactic acid, lactide, glycolic acid, glycolide, epsilon-caprolactone, 1,4-dioxan-2-one, and (1,3-dioxan-2-one).

13. The device of claim 1, wherein the rod member comprises biodegradable aliphatic polymers, copolymers, and blends formed from monomers selected from the group consisting of lactic acid, lactide, glycolic acid, glycolide, epsilon-caprolactone, 1,4-dioxan-2-one, and (1,3-dioxan-2-one).

14. The device of claim 1, wherein the cannulated anchor member comprises poly(lactic acid).

15. The device of claim 1, wherein the cord comprises poly(lactic acid).

16. The device of claim 1, wherein the rod member comprises poly(lactic acid).

17. The device of claim 1, wherein the cannulated anchor member or the cord comprises poly(lactide-co-glycolide) in a mole ratio of 95 lactic acid to 5 glycolic acid.

18. The device of claim 1, wherein the cord comprises poly(lactide-co-glycolide) in a mole ratio of 95 lactic acid to 5 glycolic acid.

19. The device of claim 1, wherein the stopper member comprises poly(epsilon-caprolactone-co-1,4-dioxan-2-one), in a mole ratio of 95 epsilon-caprolactone to 5 1,4-dioxan-2-one.

20. The device of claim 1, additionally comprising a second anchor member, a second rod member, and a second stopper member mounted to the second end of the cord.

21. A method of repairing tissue, comprising the steps of:
providing a tissue repair device, the device comprising:
a cannulated anchor member having a longitudinal passage, said passage having first and second open ends;
a flexible cord having a terminal first end and a second end, wherein the cord is slidably mounted in the passage such that the first and second ends of the cord extend, respectively, out from the first and second open ends of the passage, such that the cord is free to slide within said passage;
a rod member, the rod member mounted through the terminal first end of the cord outside of said anchor member; and,
a stopper member separate from said anchor member mounted to the first end of the cord and the rod member outside of said anchor member to prevent the terminal first end of the cord from passing back through the longitudinal passage, wherein the stopper member is molded about and melted to the rod member and the terminal first end of the cord, thereby securing the stopper member to the first end of the cord;
creating a cavity in tissue adjacent to a site of damaged tissue;
inserting at least part of the anchor member in the cavity;
engaging the damaged tissue with the cord; and,
tensioning the cord to effect a tissue repair.

* * * * *